(12) United States Patent
Kirk et al.

(10) Patent No.: US 7,796,805 B1
(45) Date of Patent: Sep. 14, 2010

(54) DEFECT DETECTION

(75) Inventors: Michael D. Kirk, Los Altos, CA (US);
Stephen A. Biellak, Sunnyvale, CA (US); David W. Shortt, Milpitas, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 1388 days.

(21) Appl. No.: 11/234,974

(22) Filed: Sep. 26, 2005

(51) Int. Cl.
*G06K 9/00* (2006.01)
(52) U.S. Cl. .................. 382/149; 382/100; 382/141; 382/145; 356/237.2; 356/237.3; 356/237.5
(58) Field of Classification Search ............ 382/100, 382/141, 145, 149; 356/512, 237.2, 237.3, 356/237.5
See application file for complete search history.

(56) References Cited

U.S. PATENT DOCUMENTS

| | | | | |
|---|---|---|---|---|
| 6,490,032 | B1 * | 12/2002 | Zhou et al. ............... | 356/237.4 |
| 7,430,898 | B1 * | 10/2008 | Weber-Grabau et al. ...... | 73/105 |
| 2007/0052939 | A1 * | 3/2007 | Ishii et al. ............... | 355/53 |

OTHER PUBLICATIONS

J. Merle Elson, *Multilayer-coated optics: guided-wave coupling and scattering by means of interface random roughness*, J. Opt. Soc. Am. A, vol. 12, No. 4, 1995, pp. 729-742.

* cited by examiner

*Primary Examiner*—Samir A. Ahmed
*Assistant Examiner*—Ali Bayat
(74) *Attorney, Agent, or Firm*—Luedeka, Neely & Graham, P.C.

(57) ABSTRACT

A wafer having improved inspection sensitivity to foreign matter on a top-most surface of the wafer, as detected with a surface scanning optical inspection system that uses an inspection wavelength. The wafer includes a substantially homogenous first layer at the top-most surface of the wafer, the first layer having a first thickness. The first layer is at least partially transparent to the inspection wavelength. A substantially homogenous second layer immediately underlies the first layer, the second layer having a second thickness. The second layer is at least partially transparent to the inspection wavelength. A substrate immediately underlies the second layer. The first thickness and the second thickness are set in a combination that produces a local minimum of an electric field at the top-most surface and a local maximum of an electric field within one hundred nanometers above the top-most surface.

16 Claims, 6 Drawing Sheets
(4 of 6 Drawing Sheet(s) Filed in Color)

DEFECT DETECTION

FIELD

This invention relates to the field of integrated circuit fabrication. More particularly, this invention relates to optical inspection of monitor wafers employed during the fabrication of integrated circuits.

BACKGROUND

Inspection is an important aspect of the fabrication process for integrated circuits. Inspection is generally used to detect imperfections in the integrated circuits, such as pattern defects, particles, or other foreign matter.

However, it is becoming ever more difficult to detect small defects on rough surfaces utilizing a dark-field scanning surface inspection system; more specifically, particles and contaminants in the range of sixty nanometers to two hundred nanometers polystyrene latex sphere (PSL) equivalent size on films used in integrated circuit processing. These films can be, for instance, polysilicon, low-k dielectrics, silicon-on-insulator, strained-silicon-on-insulator, and other similarly rough materials that are at least partially transparent to optical wavelengths.

Current methods on smooth surfaces, such as bare silicon, use oblique illumination with a polarization combination called "P-U" which indicates that the incident light is polarized (e.g. in the plane of incidence), and the collected scattered light is unpolarized, meaning that all polarizations are collected. This method achieves the greatest sensitivity on very smooth surfaces. However, rough surfaces scatter too much light in P-U, and the scattering from small defects is swamped by the surface scattering. In these cases, it is well known that the "double-dark-field" configuration is useful for inspecting rough surfaces for contamination and defects.

In particular, using s polarized obliquely incident light, e.g. polarized perpendicular to the plane of incidence, results in a dark fringe at the surface, and very little light is scattered from the surface itself. In conjunction with an analyzer oriented perpendicular to the plane of scatter, and an aperture limited to "side-angle collection," the unwanted surface background contribution can be reduced by several orders of magnitude. Large particles and defects resting on the surface can then be detected relatively easily, as they do not experience the dark fringe, and therefore they perturb (scatter) the incident electric field efficiently compared to the surface.

Side-angle collection means that the collected scattered light is limited to azimuthal angles reasonably close to plus or minus ninety degrees with respect to the plane of incidence. For example, in some instruments there are two configurations for side angle collection: one which collects light within ten degrees of plus or minus ninety degrees (twenty degrees azimuthal width on the plane of incidence) and one which collects light within twenty degrees of plus or minus ninety degrees (forty degrees azimuthal width).

These methods of S-S polarization with side-angle collection work well for particles having a size greater than approximately one-half the wavelength of the incident light. The S-S side-angle configuration is very effective at reducing the scattering from the surface. Unfortunately, it is also very effective at reducing the scattering from small defects, where small is defined as a diameter that is less than about forty percent of the wavelength of the incident light. Once the defect size increases to approximately forty percent of the wavelength of light, a typical defect begins to scatter significantly into the side-angle collector. Since the surface scattering is suppressed, this provides a significant signal-to-noise advantage.

In the past, integrated circuit fabrication processes using rough surfaces were generally subject to failure by defects having a size of approximately two hundred nanometers and larger. Such defects could be detected using an illumination wavelength of 488 nanometers, which was used at the time. However, now there is a need to detect defects having a size of less than one hundred nanometers on rough, partially transparent surfaces. Even an ultra violet wavelength of 355 nanometers is not sufficient to efficiently detect such defects when combined with the S-S side-angle technique.

Electromagnetic wave theory allows one to self-consistently calculate the electric field at every position within or above a multi-layer film structure, given the thicknesses and refractive indices of the layers. In general, fields scattered from an object are proportional to the magnitude of the incident field in the vicinity of the object. Therefore, if the incident electric field magnitude is adjusted to be relatively small at a point on the rough film surface, and substantially larger at a point that is tens of nanometers above the surface, where many defects and contaminants reside, improved defect scatter signal to rough surface scatter signal may be observed in an inspection system.

The S-S side-angle collection strategy, described above, utilizes this in part, but presumes that the rough film is opaque, and that there is very little light that is reflected from the substrate or other layer interfaces underneath the rough film. In this case, the potential for enhanced defect scattering relative to surface scattering is limited, because with only two waves interfering, namely the incoming wave and the wave reflected from the rough surface, significant changes in field strength are not possible over distances much smaller than one-half the wavelength of light.

On the other hand, if additional film layers exist between the uppermost rough film layer and the substrate, there are multiple reflected waves, which can interfere to produce dramatic differences in electric field strength near the surface of the rough film, over distances of one-tenth the wavelength of light, or smaller.

Many rough films, particularly metals, are relatively opaque at visible and ultraviolet wavelengths. However, other rough films of significance, such as polysilicon, can be relatively transparent. Also, with advanced integrated circuit processing, films can be significantly thinner than inspection wavelengths. Light can easily penetrate a polysilicon film to interact with the substrate and other films, and reflected light from these other interfaces can again traverse the polysilicon film, with only modest attenuation, to interfere at the rough surface.

What is needed, therefore, is a system that overcomes problems such as those described above, at least in part.

SUMMARY

The above and other needs are met by a wafer having improved inspection sensitivity to foreign matter on a top-most surface of the wafer, as detected with a surface scanning optical inspection system that uses an inspection wavelength. The wafer includes a substantially homogenous first layer at the top-most surface of the wafer, the first layer having a first thickness. The first layer is at least partially transparent to the inspection wavelength. A substantially homogenous second layer immediately underlies the first layer, the second layer having a second thickness. The second layer is at least partially transparent to the inspection wavelength. A substrate immediately underlies the second layer. The first thickness and the second thickness are set in a combination that produces a local minimum of an electric field at the top-most surface and a local maximum of an electric field within one hundred nanometers above the top-most surface.

By setting the thicknesses of the two layers in this manner, the background scatter due to surface roughness in the signal to noise model of the inspection system can be reduced, thus increasing the sensitivity of the inspection system, or in other words, decreasing the effective diameter of the particles and other defects that can be detected on the substrate with the inspection system.

In various embodiments, the surface scanning optical inspection system is a dark field system. The first material may be one of polysilicon, silicon, low-K dielectric, and strained silicon. Preferably, the first material is a non-metallic material. The second material may be one of an oxide and a nitride. The substrate is preferably a silicon substrate. The second layer preferably has a smooth surface.

According to another aspect of the invention there is described a method of detecting foreign matter on a top-most surface of a wafer with a surface scanning optical inspection system that uses an inspection wavelength, by selecting a substantially homogenous first material for a first layer and a substantially homogenous second material for a second layer, where each of the first material and the second material are at least partially transparent to the inspection wavelength, and forming a film stack by, forming the second layer directly on a substrate at a second thickness of only the substantially homogenous second material, and forming the first layer directly on the second layer at a first thickness of only the substantially homogenous first material, where the first thickness and the second thickness are set in a combination that produces a local minima of an electric field at the top-most surface and a local maxima of an electric field within one hundred nanometers above the top-most surface.

In a preferred embodiment, the combination of first and second thicknesses is determined according to the steps of measuring the index of refraction for the first and second materials, calculating a first electric field at the top-most surface of the film stack, plotting the first electric field as a function of the first and second thicknesses, calculating a second electric field at a desired distance above the top-most surface of the film stack, plotting the second electric field as a function of the first and second thicknesses, finding pairs of local maxima of the second electric field and local minima of the first electric field, characterizing a power spectral density of the film stack, calculating background scatter due to surface roughness of the top-most surface of the film stack, computing a signal to noise ratio for the surface scanning optical inspection system using the background scatter, plotting the signal to noise ratio as a function of the first and second thicknesses, and selecting combinations of the first and second thicknesses where the signal to noise ratio is enhanced.

According to another aspect of the invention there is described a method of detecting foreign matter on a top-most surface of a wafer with a surface scanning optical inspection system that uses an inspection wavelength, the method comprising the steps of selecting a first material for a first layer and a second material for a second layer, where each of the first material and the second material are at least partially transparent to the inspection wavelength, and forming a film stack by, forming the second layer over a substrate at a second thickness, and forming the first layer over the second layer at a first thickness, wherein the combination of first and second thicknesses is determined by, measuring the index of refraction for the first and second materials, calculating a first electric field at the top-most surface of the film stack, plotting the first electric field as a function of the first and second thicknesses, calculating a second electric field at a desired distance above the top-most surface of the film stack, plotting the second electric field as a function of the first and second thicknesses, finding pairs of local maxima of the second electric field and local minima of the first electric field, characterizing a power spectral density of the film stack, calculating background scatter due to surface roughness of the top-most surface of the film stack, computing a signal to noise ratio for the surface scanning optical inspection system using the background scatter, plotting the signal to noise ratio as a function of the first and second thicknesses, and selecting combinations of the first and second thicknesses where the signal to noise ratio is enhanced.

BRIEF DESCRIPTION OF THE DRAWINGS

The patent or application file contains at least one drawing executed in color. Copies of this patent or patent application publication with color drawings will be provided by the Office upon request and payment of the necessary fee.

Further advantages of the invention are apparent by reference to the detailed description when considered in conjunction with the figures, which are not to scale so as to more clearly show the details, wherein like reference numbers indicate like elements throughout the several views, and wherein.

DETAILED DESCRIPTION

Figure 1:
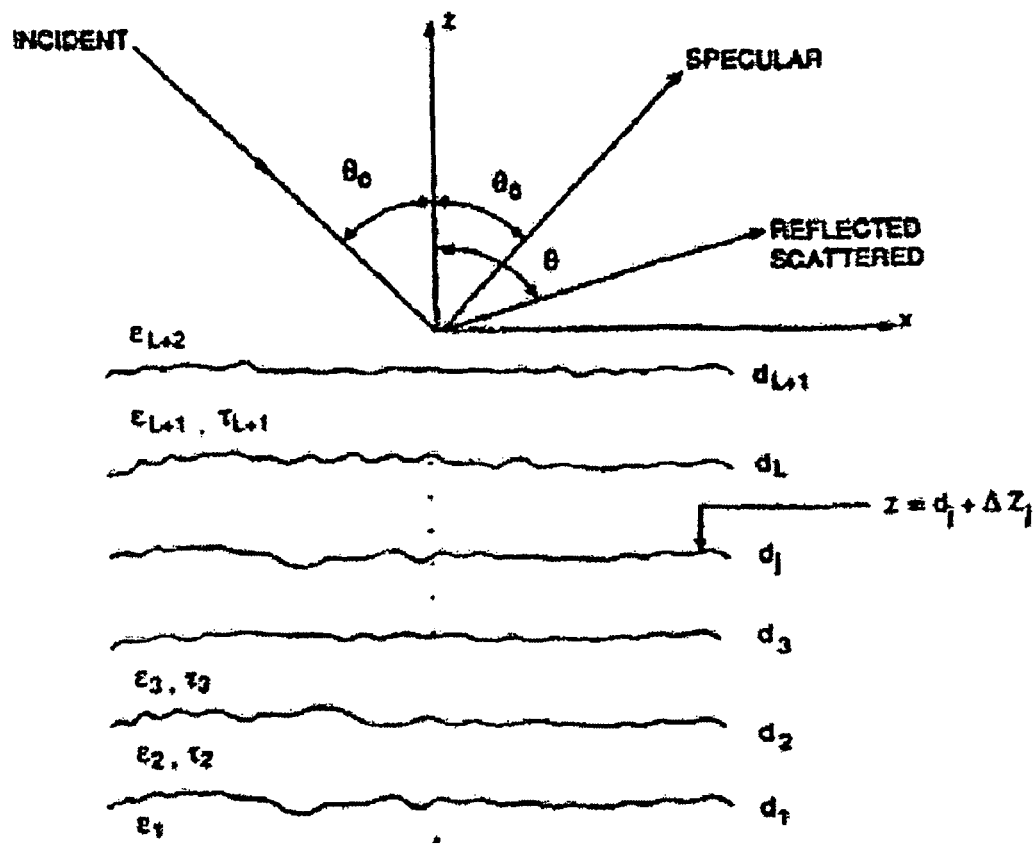
FIG. 1 is a cross sectional depiction of a multilayer rough film structure.

The methods according to the preferred embodiments of the preset invention utilize a second film that is transparent to the inspection wavelength employed, which is deposited underneath the rough film of interest. The rough film of interest is preferably polysilicon, or another partially transparent film, such as a low-K dielectric, or even a thin layer of silicon or strained silicon. The second film, if of the proper thickness, in conjunction with the attributes of the rough film, acts to enhance the signal from particles or contaminants resting on the rough surface, while suppressing scattering from the surface itself. The second film is preferably smooth, but a rough surface on the second film is also acceptable.

As used herein the term "rough" means a surface where the inspection system sensitivity is limited by speckle noise or shot noise from the random surface roughness, and not by other noise sources, including but not limited to electronics thermal noise, illumination source shot noise, and flicker noise. Therefore, different inspection systems will have slightly different levels of tolerable roughness, and as inspection systems improve, the definition of "rough" will tend to change. For current inspection systems, a rough surface is typically a surface with an isotropic rout-mean-square roughness value of one nanometer or higher, measured over the spatial frequency band 0.11 per micrometer to 3.86 per micrometer.

Similarly, a "smooth" surface is also defined in accordance with the general definition of "rough" as given above, which by current standards means a surface with an isotropic root-mean-square roughness value of 0.1 nanometer (one angstrom) or less, measured over the spatial frequency band 0.11 per micrometer to 3.86 per micrometer.

We therefore present a method to improve rough film sensitivity based not on a modification of the inspection systems, but rather on a modification of the film structure of a monitor substrate or structure. A multilayer structure, with each layer having an appropriate thickness, can provide significant sensitivity enhancement for rough film monitoring.

The embodiment considered in this disclosure is a single additional oxide film underneath the polysilicon film, deposited on a silicon substrate. The monitor film structure, from top to bottom, is (1) a rough native oxide film, (2) a rough polysilicon film, (3) an oxide film (oxides are generally smooth, though, for example, if the oxide was polished using chemical-mechanical polishing, it could be rough), and (4) a silicon substrate.

The two films described herein are preferably formed of substantially homogenous materials. Thus, while one or both of the layers may be formed of a combination of materials, these materials are not formed into separately identifiable strata of substantially different composition or structure. Rather, these materials are substantially homogenous in composition and structure throughout the given film layer.

This technique is especially applicable to polysilicon, in that the polysilicon refractive index is typically very close to that of silicon. Therefore, a polysilicon film-silicon substrate structure does not have much variation in scatter properties as a function of polysilicon thickness. On the other hand, a polysilicon film on oxide film on silicon substrate structure admits much larger changes in scatter properties as the film thicknesses change. Thus, this technique has special applicability to detecting or otherwise measuring relatively small particles on top of polysilicon layers, such as might be formed directly on a silicon substrate in prior art integrated circuit fabrication flows.

A polysilicon monitor wafer that is currently inspected on an inspection system at a one hundred-ninety nanometer PSL equivalent sensitivity, can potentially be inspected on the same system at a sensitivity of one hundred and thirty nanometers or better, if the teachings of the present invention are applied to make small adjustments to the layer thicknesses. Other dark-field inspection systems, with a sensitivity of one hundred-two nanometers, can potentially be improved to a sensitivity of ninety-five nanometers or better through similar means.

The expected PSL-equivalent sensitivity of two dark-field systems inspecting a multilayer rough polysilicon monitor wafer can be computed and compared to experimental results. These calculations are generated using well-known PSL scattering analysis developed at KLA-Tencor by Stokowski and elsewhere by Bobbert and Vlieger (P.A. Bobbert and J. Vlieger, "Light scattering by a sphere on a substrate," Physica 137A, 209-242 (1986)), and the theoretical description of rough-surface scattering from Rice, extended by J. M. Elson in, "Multilayer-coated optics: guided-wave coupling and scattering by means of interface random roughness," J. Opt. Soc. Am. A 12(4) 729 (1995).

With first-order vector perturbation theory, Rice derived the expected scattering of a surface as a function of input and output polarization, wavelength, refractive index, and power-spectral-density. Elson generalized the result to multiple rough layers on top of any substrate. In Elson's formalism, each layer can have roughness correlated with other layers (i.e. conformal roughness), uncorrelated roughness (non-conformal), or can be smooth. To apply Elson's formulae, the statistical properties of the roughness must be well-characterized (for instance with Atomic Force Microscope measurements) and the layer refractive indices and thickness must also be well known (for instance, after measurement with spectroscopic ellipsometry). The general film structure analyzed is shown in FIG. 1.

Multi-layer scatter theory is applied to model the inspection of a customer wafer of interest. Using spectroscopic ellipsometry and AFM analysis, the film thicknesses, refractive indices, and the power spectral density of the roughness is characterized. The polysilicon typically has a thin native oxide layer on top, which can be assumed to have a roughness correlated to that of the polysilicon, due to the small thickness of the native oxide layer, which is typically no more than about fifty angstroms.

For two inspection systems of interest, there exist dramatic variations in expected PSL sensitivity as a function of polysilicon thickness and oxide thickness. These results are illustrated in the two-dimensional plots of FIGS. 2 and 3.

Figure 2:
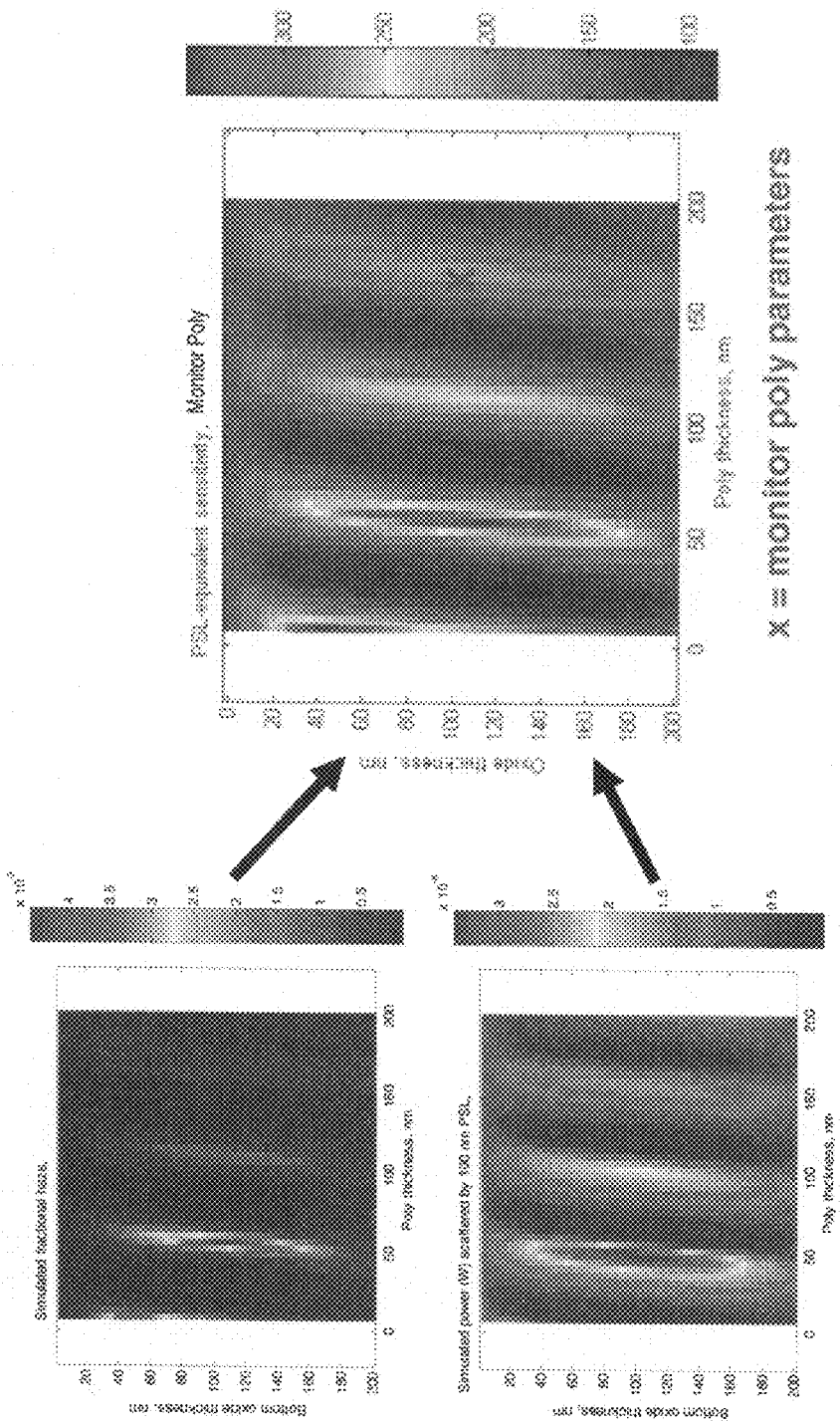
FIG. 2 contains plots of expected PSL sensitivity of a first inspection system as a function of polysilicon thickness and oxide thickness.

FIG. 2 depicts the expected haze or surface scatter in the upper left and the expected one hundred nanometer PSL scatter in the lower left from a rough poly film with an oxide under layer, inspected on the first test system. On the right is the expected PSL equivalent sensitivity of the first test system. The x-axis in all plots is the polysilicon film thickness in nanometers, and the y-axis is the underlying oxide film thickness in nanometers. The shading corresponds to the expected sensitivity or signal. A native oxide layer was present on top of the polysilicon. It is noted that the haze and the PSL scatter signals are slightly "out of phase" with each other. This characteristic provides a basis of the present invention.

Figure 3:
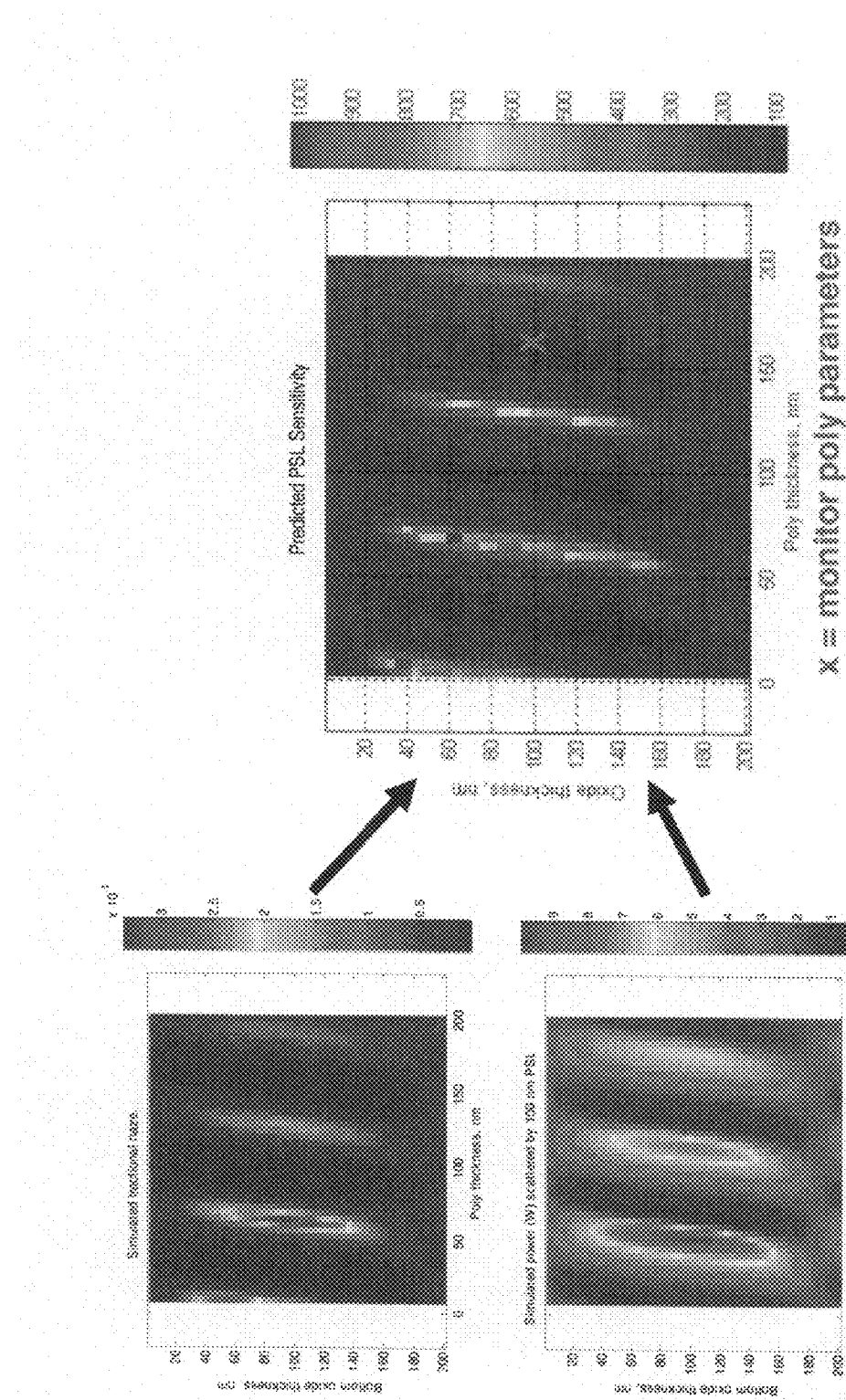
FIG. 3 contains plots of expected PSL sensitivity of a second inspection system as a function of polysilicon thickness and oxide thickness.

FIG. 3 depicts the expected haze or surface scatter in the upper left and the expected one hundred nanometer PSL scatter in the lower left from a rough polysilicon film with an oxide under layer, inspected on the second test system. On the right is the expected PSL equivalent sensitivity of the second system. The x-axis in all plots is the polysilicon film thickness in nanometers, and the y-axis is the underlying oxide film thickness in nanometers. The shading corresponds to the expected sensitivity or signal. A native oxide layer was present on top of the polysilicon. It is noted that the haze and the PSL scatter signals are again slightly "out of phase" with each other.

The actual thicknesses of the films on the wafer used to seed this model were one hundred and sixty-four nanometers and one hundred and one nanometers for the polysilicon and oxide, respectively. This corresponds to a PSL sensitivity of about one hundred and ninety nanometers on the system as shown in FIG. 2, and a sensitivity of about one hundred and two nanometers on the system as shown in FIG. 3. As can be seen in the scan results in FIG. 4, this matches closely with experiments.

Figure 4:
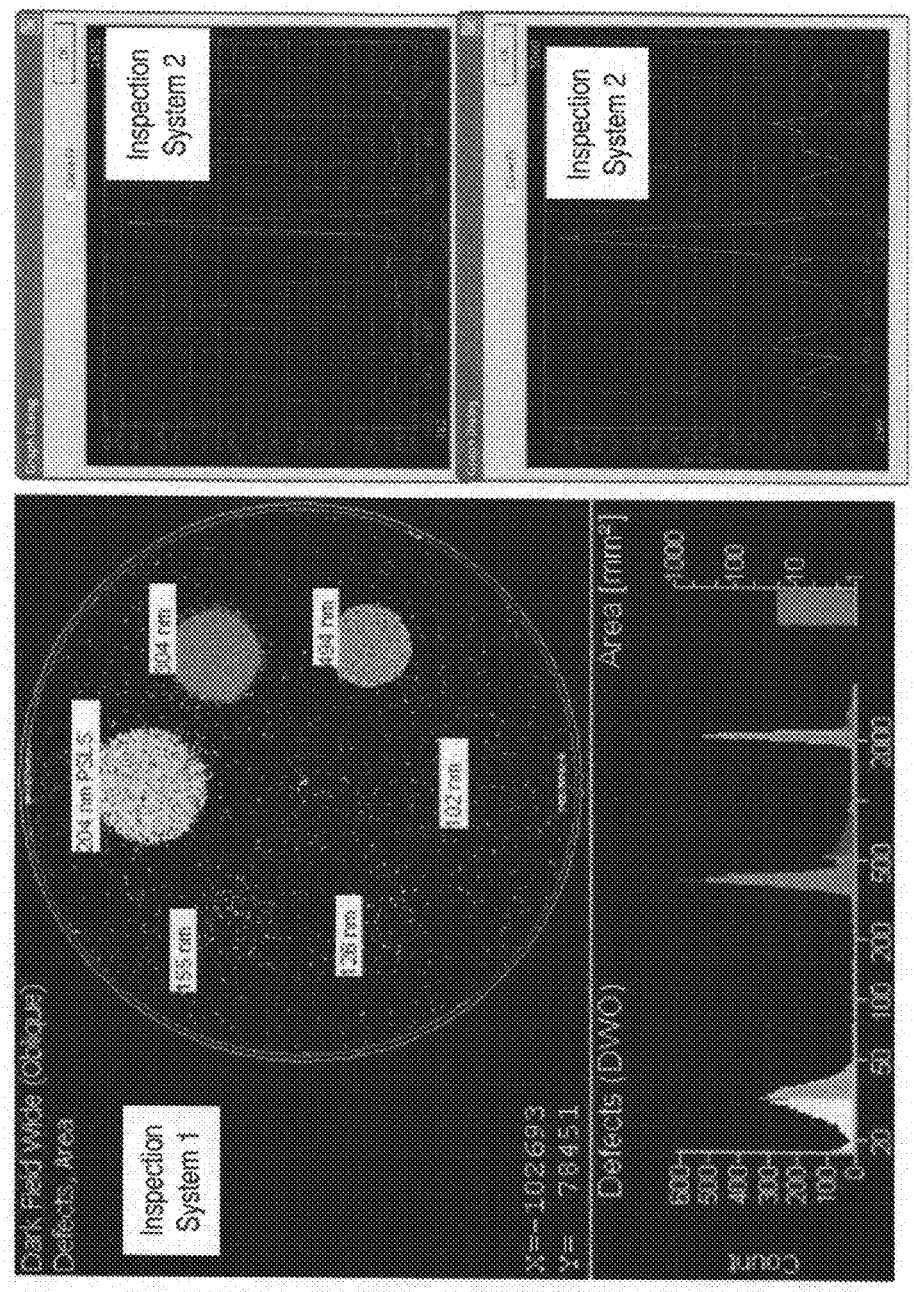
FIG. 4 depicts actual scan results for the first and second inspection systems.

FIG. 4 depicts the inspection performance of the two dark-field systems on a multilayer rough poly film wafer. On the left is a capture map from the first test system, illustrating full capture of a "spot deposition" of two hundred and four nanometer PSLs, but little capture of a spot deposition of one hundred and fifty-five nanometer PSLs. The predicted performance on this wafer, using the modeling developed for this disclosure, was one hundred and ninety nanometers. On the right are two PSL traces captured on the second test system, of one hundred and twenty-six nanometers and one hundred and two nanometers. The predicted system performance was one hundred and two nanometers, again a good agreement with theory.

According to the modeling, the second system appears to be well suited to inspect this particular monitor wafer, as FIG. 3 indicates the PSL sensitivity is relatively close to a minimum. However, FIG. 2 suggests that the first system is far from optimal sensitivity on this wafer due to the particular thicknesses of the layers. If, instead of a polysilicon thickness of one hundred and sixty-four nanometers, a polysilicon thickness of one hundred and forty-four nanometers is used, the sensitivity of the first system could potentially improve from one hundred and ninety nanometers to one hundred and thirty nanometers or better. For the second system, a similar polysilicon thickness change could improve the inspection sensitivity from one hundred and two nanometers to about ninety-five nanometers.

Figure 5:
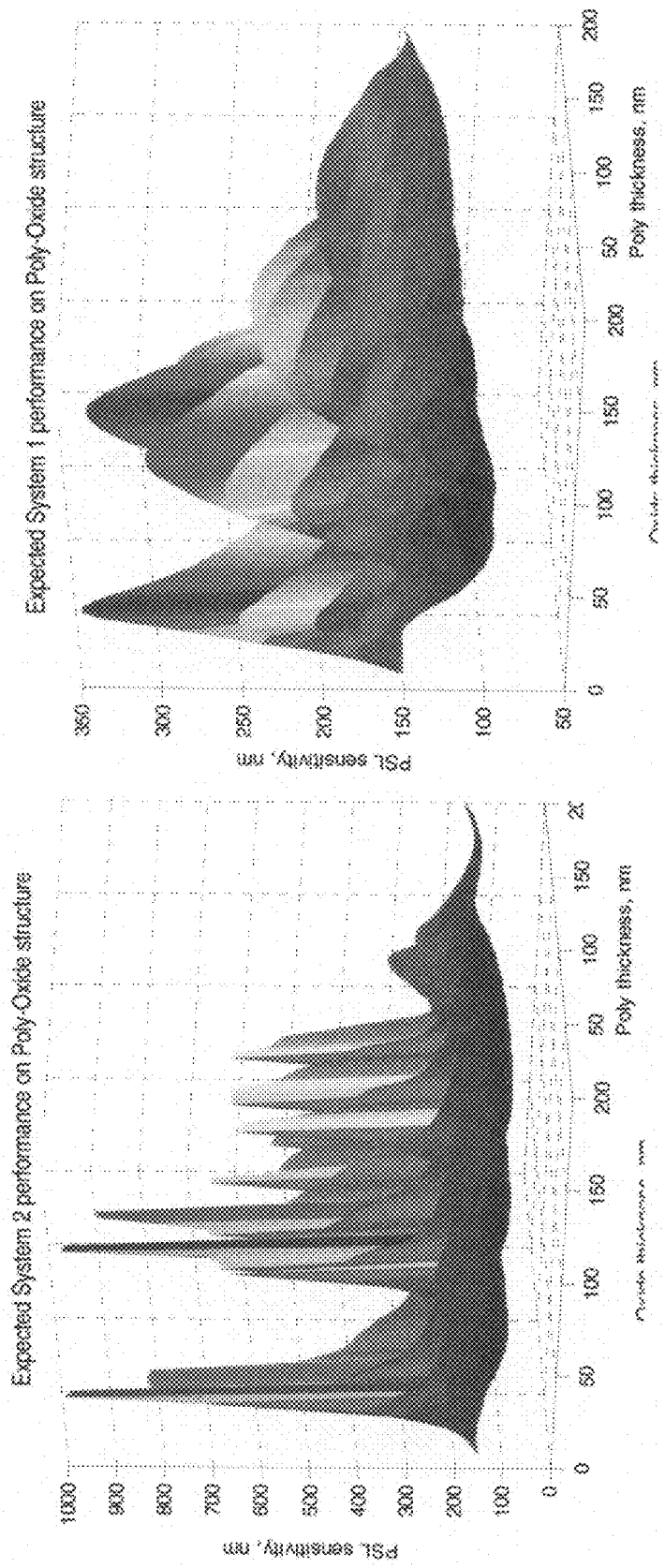
FIG. 5 depicts three dimensional plots of the expected PSL sensitivity for the first and second inspection systems as functions of polysilicon thickness and oxide thickness.

In FIG. 5, three dimensional perspectives of the sensitivity plots of FIGS. 2 and 3 are shown. More significant adjustments of polysilicon and oxide layer thicknesses on this particular monitor wafer can yield sensitivities on the order of eighty nanometers. On the left of FIG. 5 it is seen that the performance of the first test system on this rough polysilicon film could potentially be eighty-one nanometers, given optimized layer thicknesses, and on the right the performance of the second test system could potentially be eighty-six nanometers.

These methods are generally applicable to any surface inspection system utilizing any wavelength or angle of incidence, or multiple wavelengths, or a plurality of incidence angles, and a collector responsive to scattered light. The input beam may be stationary, or it may be scanned. The system may be imaging, or non-imaging.

The embodiments of the invention can be easily implemented on various inspection systems. Polarization, wavelength, and incidence angle do not restrict its use, though for particular films, some test system architectures may be more advantageous than others. For instance, a visible system may derive more benefits from this methodology on polysilicon than an ultra violet system, as the ultra violet wavelengths are absorbed much more strongly than visible wavelengths, and therefore less effective interference conditions are obtained on ultra violet systems.

Figure 6:
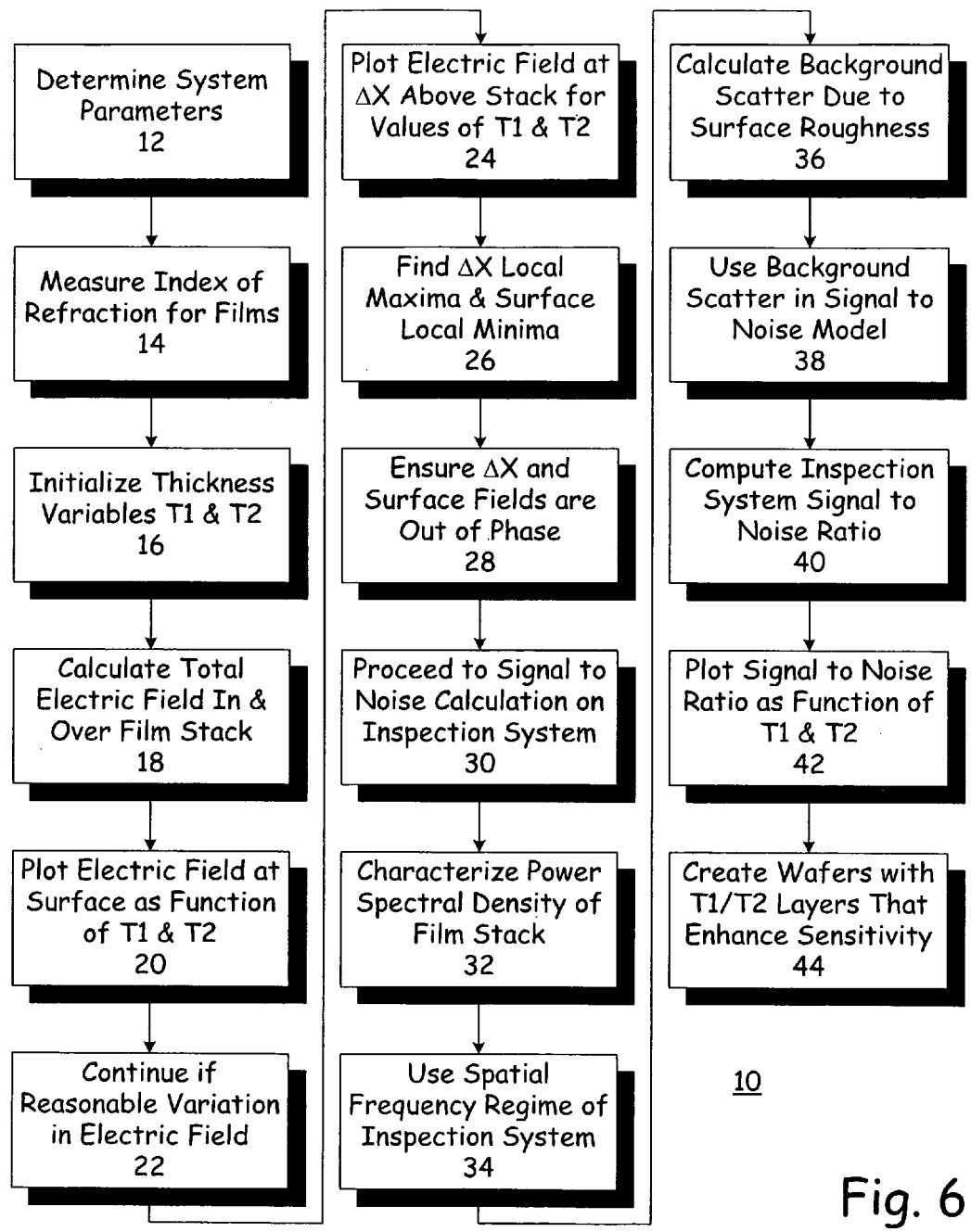
FIG. 6 depicts a flow chart of a method for determining polysilicon and oxide thicknesses according to a preferred embodiment of the present invention.

FIG. 6 depicts a flow chart of a method 10 for determining polysilicon and oxide thicknesses according to a preferred embodiment of the present invention. The first step is to determine wafer inspection system wavelength(s) of operation and angle(s) of incident light and input polarization state (s), as given in block 12. Next, the real and complex indices of refraction of the two films of interest (and the substrate and any native top surface oxide) are measured at the inspection system wavelength(s), using a well known technique such as, for instance, spectroscopic ellipsometry, as given in block 14.

An assumption is made that the two films (in this example, the polysilicon layer and the underlying oxide layer) have two unknown (or adjustable) thicknesses, t1 and t2, as given in block 16. The total electric field inside and above the film stack is calculated, such as by using the well-known Fresnel equations, using the above information, as given in block 18. The magnitude of the electric field at the surface of the top layer is preferably plotted as a function of t1 and t2, which are the two film thicknesses as defined above, as given in block 20. If the electric field magnitude varies substantially for reasonable values of t1 and t2 (meaning, for example, that the thicknesses are allowable within the given semiconductor fabrication process to be monitored), then the process is continued, as given in block 22. If not, the process is stopped in favor of another method, as this method may not be the most efficient method in such situations.

The magnitude of the electric field at from about thirty nanometers to about fifty nanometers above the top surface ($\Delta X$) is plotted as a function of the two thickness parameters, t1 and t2, as given in block 24. If there are any combinations of t1 and t2 where the electric field at from about thirty nanometers to about fifty nanometers above the surface is at or near a local maxima and the electric field at the surface is at or near a local minima, then these thickness combinations are the preferred values for enhanced defect detection, as given in block 26. If such values of t1 and t2 are found, then this method is useful. If the fields at the surface and the fields at from about thirty nanometers to about fifty nanometers above the surface rise and fall in tandem, rather than "out of phase," as given in block 28, then the present method is preferably stopped in favor of another method, as this method may not be the most efficient method in such situations.

If this method meets the criteria given above, then a full signal-to-noise wafer inspection system calculation is preferably accomplished, as commenced in block 30. The Power Spectral Density of the film stack of interest is preferably characterized, most preferably by an Atomic Force Microscope, as given in block 32. It is preferred that the Power Spectral Density is measured over the spatial frequency regime that is sampled by the wafer inspection system to be employed, typically on the order of from about one-tenth inverse micrometers to about four inverse micrometers, as given in block 34.

Once the Power Spectral Density of the surface is known, the equations as provided in the Elson reference above may be employed, in conjunction with the measurements made in the steps above, to determine the background scatter due to film stack surface roughness, as given in block 36. The background scatter due to film stack surface roughness is then ready to be employed in the wafer inspection system signal to noise model, as given in block 38. The inspection system signal to noise is then predicted, which uses parameters of the inspection system of interest as input, including but not limited to noise sources (thermal, shot, analog-to-digital-conversion), inspection system geometry (imaging or non-imaging, solid angles of collection, point spread function), source and sensor characteristics (quantum efficiency, power, size), analog and digital electronic layout, and algorithm and software design, as given in block 40.

The signal to noise is then plotted as a function of the two thickness parameters, t1 and t2, as given in block 42. If a substantial advantage (typically, five to ten nanometers of PSL-equivalent sensitivity) can be obtained from one thickness combination t1, t2 over other combinations, then that thickness combination is preferably selected for the semiconductor monitor process, as given in block 44.

The method can be implemented by adjusting the thicknesses of the two layers as deposited on standard, production wafers that are moving through the fabrication process. Alternately, the method can be implanted by forming monitor wafers that have the proper thickness of the second layer deposited on them, which are then placed into the process whereby the first layer is formed on production wafers. The monitor wafers are then inspected with the optical system according to the present invention to detect problems with particles and other contamination or defects in the process.

In summary, these methods improve inspection sensitivity to foreign matter on top of partially transparent rough films utilizing a surface scanning dark-field optical system. A rough film where sensitivity improvement is obtained has the following characteristics: it is deposited on a substrate and is at least partially transparent to the illumination wavelength of interest. Furthermore, one or more additional transparent layers are deposited between the rough surface to be inspected and the substrate. The deposition thicknesses of the layers are adjusted to minimize the electric field at the surface of the top rough layer, while at the same time, maintaining a substantial electric field some number of nanometers above the surface. These optimal thicknesses tend to be dependent on the refractive indices of the layers at the wavelength of interest, the roughness characteristics of the rough surface, and the inspection system geometry. Once the layer thicknesses are adjusted in this manner, the sensitivity of the dark-field scanning system to particles and contaminants resting above the mean surface of the rough film is improved, and preferably optimized.

The foregoing description of preferred embodiments for this invention has been presented for purposes of illustration and description. It is not intended to be exhaustive or to limit the invention to the precise form disclosed. Obvious modifications or variations are possible in light of the above teachings. The embodiments are chosen and described in an effort to provide the best illustrations of the principles of the invention and its practical application, and to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

What is claimed is:

1. A wafer having improved inspection sensitivity to foreign matter on a top-most surface of the wafer, as detected with a surface scanning optical inspection system that uses an inspection wavelength, the wafer comprising:
    a substantially homogenous first layer at the top-most surface of the wafer, the first layer having a first thickness, where the first layer is at least partially transparent to the inspection wavelength,
    a substantially homogenous second layer immediately underlying the first layer, the second layer having a second thickness, where the second layer is at least partially transparent to the inspection wavelength, and
    a substrate immediately underlying the second layer,
    where the first thickness and the second thickness are set in a combination that produces a local minimum of an electric field at the top-most surface and a local maximum of an electric field within one hundred nanometers above the top-most surface.

2. The wafer of claim 1, wherein the surface scanning optical inspection system is a dark field system.

3. The wafer of claim 1, wherein the first layer is one of polysilicon, silicon, low-K dielectric, and strained silicon.

4. The wafer of claim 1, wherein the first layer is a non-metallic material.

5. The wafer of claim 1, wherein the second layer is one of an oxide layer and a nitride layer.

6. The wafer of claim 1, wherein the substrate is a silicon substrate.

7. The wafer of claim 1, wherein the second layer has a smooth surface.

8. The wafer of claim 1, wherein the top-most surface of the first layer has a rough surface.

9. A method of detecting foreign matter on a top-most surface of a wafer with a surface scanning optical inspection system that uses an inspection wavelength, the method comprising the steps of:
    selecting a substantially homogenous first material for a first layer and a substantially homogenous second material for a second layer, where each of the first material and the second material are at least partially transparent to the inspection wavelength, and
    forming a film stack by,
        forming the second layer directly on a substrate at a second thickness of only the substantially homogenous second material, and
        forming the first layer directly on the second layer at a first thickness of only the substantially homogenous first material,
    where the first thickness and the second thickness are set in a combination that produces a local minimum of an electric field at the top-most surface and a local maximum of an electric field within one hundred nanometers above the top-most surface.

10. The method of claim 9, wherein the combination of first and second thicknesses is determined according to the steps of:
    measuring the index of refraction for the first and second materials,
    calculating a first electric field at the top-most surface of the film stack,
    plotting the first electric field as a function of the first and second thicknesses,
    calculating a second electric field at a desired distance above the top-most surface of the film stack,
    plotting the second electric field as a function of the first and second thicknesses,
    finding pairs of local maxima of the second electric field and local minima of the first electric field,
    characterizing a power spectral density of the film stack,
    calculating background scatter due to surface roughness of the top-most surface of the film stack,
    computing a signal to noise ratio for the surface scanning optical inspection system using the background scatter,
    plotting the signal to noise ratio as a function of the first and second thicknesses, and
    selecting combinations of the first and second thicknesses where the signal to noise ratio is enhanced.

11. The method of claim 9, wherein the surface scanning optical inspection system is a dark field system.

12. The method of claim 9, wherein the first material is one of polysilicon, silicon, low-K dielectric, and strained silicon.

13. The method of claim 9, wherein the first material is a non-metallic material.

14. The method of claim 9, wherein the second material is one of an oxide and a nitride.

15. The method of claim 9, wherein the substrate is a silicon substrate.

16. The method of claim 9, wherein the second layer has a smooth surface.

* * * * *